US 6,565,838 B1

(12) United States Patent
Carroll et al.

(10) Patent No.: US 6,565,838 B1
(45) Date of Patent: May 20, 2003

(54) SKIN REFINING COMPOSITION AND APPLICATOR

(76) Inventors: Thomas E. Carroll, 2020 Main St., South Belmar, NJ (US) 07719; Ralph J. Cataneo, 1169 E. 21st St., Brooklyn, NY (US) 11210

( * ) Notice: Subject to any disclaimer, the term of this patent is extended or adjusted under 35 U.S.C. 154(b) by 0 days.

(21) Appl. No.: 10/279,712

(22) Filed: Oct. 24, 2002

Related U.S. Application Data

(60) Provisional application No. 60/335,458, filed on Oct. 31, 2001.

(51) Int. Cl.[7] .......................... A61K 7/08; A61K 7/075; A61K 9/00; A61K 6/00
(52) U.S. Cl. .................. 424/70.19; 424/400; 424/401; 424/70.21; 424/70.31
(58) Field of Search ................................ 424/400, 401, 424/70.19, 70.21, 70.31

(56) References Cited

U.S. PATENT DOCUMENTS

| 3,533,955 | A | * | 10/1970 | Pader |
| 3,718,609 | A | * | 2/1973 | Weimer |
| 3,810,478 | A | * | 5/1974 | Olson et al. |
| 6,429,177 | B1 | * | 8/2002 | Williams et al. |

* cited by examiner

*Primary Examiner*—Thurman K. Page
*Assistant Examiner*—Humera N. Sheikh

(57) ABSTRACT

A skin refining composition contains five surfactants: sodium lauryl ether sulfate, cocoamidopropylbetaine, decyl polyglucoside, sucrose cocoate, and an amphoteric detergent. The composition also contains a sub-micron conditioning emulsion. The emulsion contains a silicone, a moisturizer, a humectant, and glycerin. The composition cleanses, exfoliates, and conditions the skin. The composition is applied with an applicator containing a foam pad and an integral brush having tapered bristles.

7 Claims, 1 Drawing Sheet

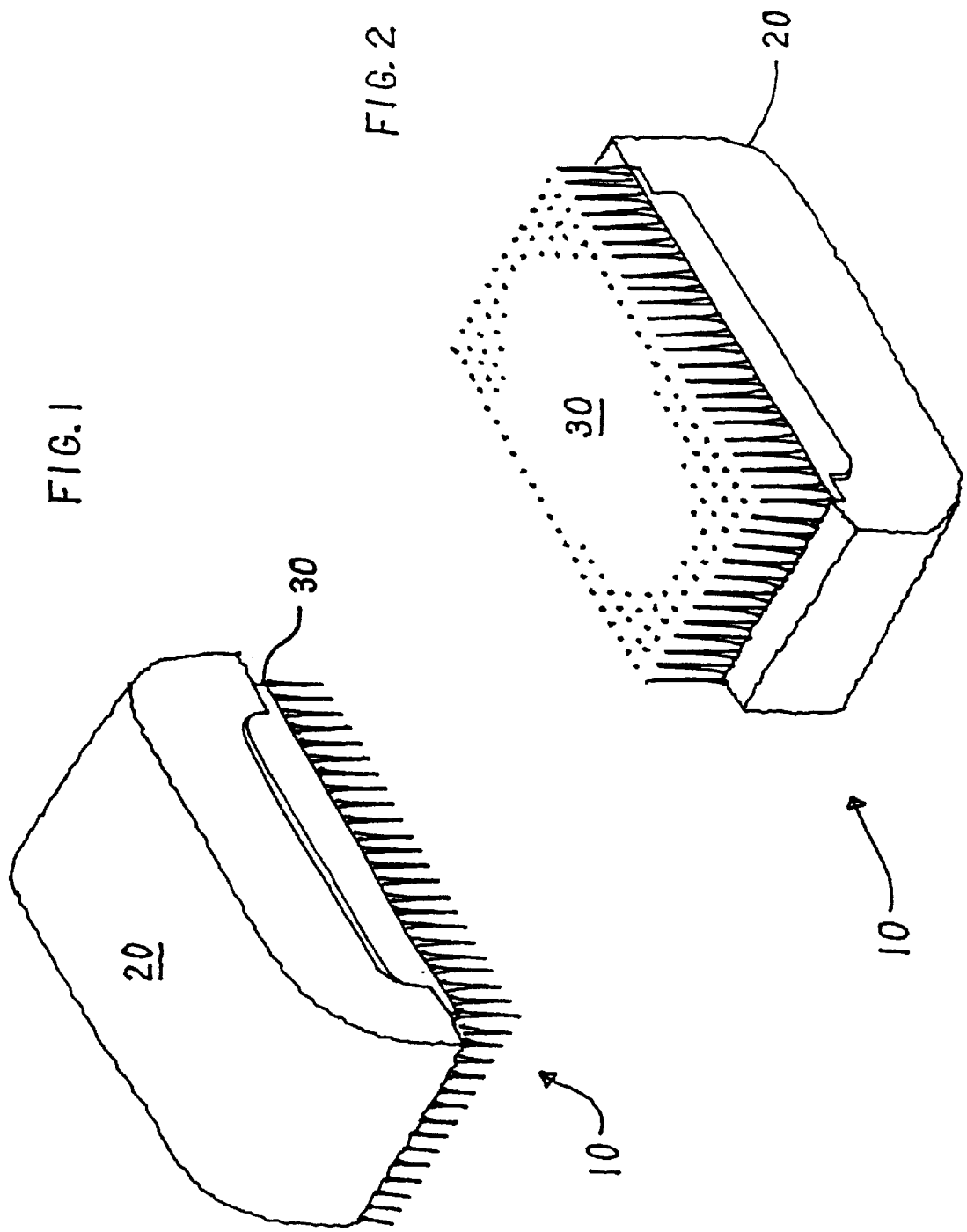

SKIN REFINING COMPOSITION AND APPLICATOR

FIELD OF THE INVENTION

This invention relates to cosmetics. More particularly, this invention relates to a skin refining system comprising a formulation, an applicator containing the formulation, and a method of refining the skin using the formulation.

BACKGROUND OF THE INVENTION

A variety of products are used for cleaning and exfoliating the skin. Most contain harsh abrasives and acids which can damage the skin. These products are typically applied with wet washcloths, non-woven paper towels, natural sponges having varying sizes of open cells, and the like. These applicators create uneven dispersion of abrasive particles, non-uniform distribution of the product on the skin, and uneven pressure on the skin. Such non-uniformity results in localized irritation of the skin.

REFERENCES CITED
U.S. PATENT DOCUMENTS

| | | | |
|---|---|---|---|
| 6,451,327 | Sep. 17, 2002 | Nakagaki, et al | 424/401 |
| 6,376,438 | Apr. 23, 2002 | Rosenberger, et al | 510/139; 510/138 |
| 6,289,547 | Sep. 18, 2001 | Narula, et al | 15/167.3 |
| 5,730,991 | Mar. 24, 1998 | Rapaport | 424/401 |
| 6,184,247 | Feb. 06, 2001 | Schneider | 514/474 |

U.S. Pat. No. 6,451,327; U.S. Pat. No. 6,376,438 describe compositions that contain abrasive particles which can cause skin damage and itching.

U.S. Pat. No. 6,289,547 describes a sponge that includes a brush with bristles used by surgeons to clean hands and arms and optionally can contain cleansing agent within the sponge.

U.S. Pat. No. 6,184,247 describes a composition that includes ascorbic acid derivatives, e.g., ascorbyl palmitate used as skin exfoliants.

U.S. Pat. No. 5,730,991 describes a composition, method and kit for at home chemical skin peeling using lower concentrations of active ingredients such as alpha hydroxy acids, salicylic acid and lactic acid.

None of the cited patents contain or describe technology or method that gently cleanses, exfoliates and conditions the skin, refining it in a single operation.

Accordingly, there is a demand for a skin refining system that cleans, exfoliates, and conditions the skin without the use of harsh abrasives and acids. There is also a demand for a skin refining system that is applied uniformly.

SUMMARY OF THE INVENTION

The general object of this invention is to provide an improved skin refining system. A more particular object is to provide an improved skin refining composition. Another more particular object is to provide an improved skin refining applicator. Another more particular object is to provide an improved method of refining the skin.

We have invented an improved skin refining composition. The composition comprises (a) about 15 to 40 percent sodium lauryl ether sulfate; (b) about 2 to 8 percent cocoamidopropylbetaine; (c) about 2 to 8 percent decyl polyglucoside; (d) about 3 to 5 percent sucrose cocoate; (e) about 3 to 5 percent amphoteric detergent; and (f) about 2 to 5 percent of a sub-micron conditioning emulsion. The conditioning emulsion comprises: (i) a silicone; (ii) a moisturizer; (iii) a humectant; and (iv) glycerin.

We have also invented an improved skin refining applicator. The applicator comprises a foam pad and an integral brush having tapered bristles, the foam pad containing the skin refining composition described above.

We have further invented an improved method of refining the skin. The method comprises applying the skin refining composition described above to the skin with a foam pad and then scrubbing the skin with a brush having tapered bristles.

The skin refining system of this invention provides a gentle cleansing, exfoliating, and conditioning of the skin.

BRIEF DESCRIPTION OF THE DRAWINGS

FIG. 1 is a perspective view of a preferred embodiment of the applicator of this invention showing the foam side on top.

FIG. 2 is a perspective view of a preferred embodiment of the applicator of this invention showing the brush side on top.

DETAILED DESCRIPTION OF THE INVENTION

This skin refining formulation of this invention comprises five surfactants: sodium lauryl ether sulfate, cocoamidopropylbetaine, decyl polyglucoside, sucrose cocoate, and an amphoteric detergent. It also comprises a sub-micron conditioning emulsion comprising a silicone, a moisturizer, a humectant, and glycerin. Each of these components is discussed in turn. All percentages herein are based on weight.

Sodium lauryl ether sulfate is a common surfactant. Surfactants are compounds that reduce surface tension when dissolved in aqueous solutions. On a molecular level, surfactants are characterized by having both hydrophilic and lipophilic portions. The hydrophilic portion is typically a polar component which is attracted to the highly polar water molecule. The lipophilic portion is typically a non-polar component which is attracted to non-polar fats and greases. Surfactants are used as cleansers because they adhere to fats and greases while also remaining in the aqueous phase. Sodium lauryl ether sulfate is generally present in the composition in an amount of about 15 to 40 percent.

Cocoamidopropylbetaine is a common surfactant. It is generally present in the composition in an amount of about 2 to 8 percent.

Polyglucosides are common surfactants. They have the general formula R-O-(G)n where R is a long chain alkyl group, G is a glucose unit, and n is the number of glucose units. Polyglucosides are typically prepared by reacting starch derivatives with fatty alcohols. A preferred polyglucoside is decyl polyglucoside. The decyl polyglucoside is generally present in the composition in an amount of about 2 to 8 percent.

Sucrose cocoate is a gentle, skin softening surfactant. It is generally present in the composition in an amount of about 3 to 5 percent.

Amphoteric detergents are compounds that are capable of behaving as either an acid or a base. A preferred amphoteric detergent is MIRANOL C2M, a disodium cocoamphodiacetate. The amphoteric detergent is generally present in the composition in an amount of about 3 to 5 percent.

The sub-micron conditioning emulsion is generally present in the composition in an amount of about 2 to 5 percent. The emulsion comprises a silicone, a moisturizer, a humectant, and glycerin. Silicones are organosiloxane polymers. A preferred silicone is dimethicone. A silicone is generally present in the emulsion in an amount of about 0.5 to 2 percent. Moisturizers are substances that restrict the loss of water by moisture vapor transmission of the skin. Suitable moisturizers include esters and emollient oils such as isopropylmyristate, isopropylpalmitate, and octylpalmitate. A moisturizer is generally present in the emulsion in an amount of about 5 to 10 percent. Humectants are substances that have an affinity for water. A preferred humectant is propylene glycol. A humectant is generally present in the emulsion in an amount of about 2 to 5 percent. Glycerin is both a moisturizer and a humectant. It augments the action of the moisturizer and the humectant in the emulsion. It is generally present in the emulsion in an amount of about 2 to 5 percent.

The skin refining composition typically contains additional components, including cocoamide monoethanolamine, a fragrance, a fragrance solubilizer, a preservative, color and deionized water.

Other ingredients can be added to the skin refining composition to provide additional properties. For example, products that color, tint, lighten, or brighten the skin can be added, as well as anti-bacterial agents.

The skin refining composition has a pH of about 5 to 7, preferably about 5.5 to 6.5, which is close to the natural pH of the skin. The composition is a clear solution having a viscosity of about 500 to 2,000 centipoise. It has a solids level of about 14 to 25 percent. The composition is an effective cleanser and exfoliator. It also leaves moisturizing ingredients which adhere to the skin to provide an overall soft and smooth finish lasting up to about 24 hours.

The skin refining composition is preferably applied to the skin with an applicator comprising a foam pad and integral brush having tapered bristles. A preferred applicator 10 is shown in FIGS. 1 and 2. The applicator contains a foam block 20 which is attached to a brush 30. The applicator is similar to surgical scrub units commonly used by medical personnel prior to surgery. The applicator preferably has a length of about 3 to 4 inches, a width of about 2 inches, a depth of about 1 to 2 inches. The foam is made up of uniform open window cells which evenly disperse the composition within the foam and onto the skin. The foam is preferably made of polyurethane. The brush bristles are fine, hair-like tapered extensions having a length of about one-half inch. Due to the tapered extensions, the bristles apply controllable uniform pressure to the skin. The bristles allow for the maximum acceptable level of dead skin removal without damage to viable skin. The brush is preferably made of high density polyethylene. The foam pad of the applicator is preferably pre-moistened with the skin refining composition After the pre-moistened composition is used, additional composition can be added by the consumer.

The massaging action of the brush, with the foaming action of the composition, scrubs away excess oils and dried surface skin cells. The action also opens and deep cleans pores to remove embedded grease. The use of the composition with the brush promotes micro circulation and healthier, brighter, more even skin tone. As a result, the skin feels softer and smoother.

An alternate embodiment of the applicator includes a foam pad with a woven mesh covering having mild abrasive characteristics.

Another alternate embodiment of the applicator includes a foam pad within a hand mitt made of a non-woven compressed natural fiber.

EXAMPLE 1

This example illustrates two formulations. The first formulation is for a body skin cleanser that has a viscosity of about 500 to 2,000 centipoise, a pH of about 5.5 to 6.5, and a solids level of about 20 to 25 percent. The second formulation is for a facial cleanser that has a viscosity of about 500 to 2,000 centipoise, a pH of about 5.5 to 6.5, and a solids level of about 14 to 17 percent.

| Ingredient | Body Skin (%) | Facial (%) |
| --- | --- | --- |
| Sodium lauryl ether sulfate | 35 | 18 |
| Cocoamidopropylbetaine | 7 | 3 |
| Decyl polyglucoside | 7 | 3 |
| Sucrose cocoate | 4 | 4 |
| Amphoteric detergent | 4 | 4 |
| Sub-micron emulsion | 3 | 4 |
| Cocoamide monoethanolamine | 2 | 2 |
| Fragrance solubilizer | 2 | 2 |
| Fragrance | 2 | 2 |
| Preservative | 1 | 1 |
| Color | qs | qs |
| Deionized water | qs 100 | qs 100 |

We claim:

1. A skin refining composition comprising:

(a) about 15 to 40 percent sodium lauryl, ether sulfate;
   (b) about 2 to 8 percent cocoamidopropylbetaine;,
   (c) about 2 to 8 percent decyl polyglucoside;
   (d) about 3 to 5 percent sucrose cocoate;
   (e) about 3 to 5 percent amphoteric surfactant; and
   (f) about 2 to 5 weight percent of a sub-micron conditioning, emulsion comprising:
      (i) a silicone; about 0.5 to 2 percent
      (ii) a moisturizer; about 5 to 10 percent
      (iii) a humectant; about 2 to 5 percent
      (iv) glycerin; about 2 to 5 percent.

2. The skin refining composition of claim 1 additionally comprising:

(i) cocoamide monoethanoloamine
   (ii) afragrance
   (iii) a fragrance solubilizer
   (iv) a preservative
   (v) color
   (vi) deionized water.

3. A skin refining applicator comprising a foam pad and an integral, brush having tapered bristles, the foam pad containing the, skin refining composition of claim 1.

4. The foam pad of the applicator of claim 3 wherein the composition is presented within individual packages.

5. A method of refining the skin comprising applying the skin refining composition of claim 1 to the skin with a foam pad and then scrubbing the skin with a brush having tapered bristles.

6. An applicator comprising a foam pad with a woven mesh covering having mild abrasive characteristics and the composition of claim 1.

7. An applicator comprising a foam pad within a hand mitt made of non-woven compressed fiber and the composition of claim 1.

* * * * *